(12) United States Patent
Sanchez et al.

(10) Patent No.: US 9,775,833 B2
(45) Date of Patent: Oct. 3, 2017

(54) METHOD FOR THE TREATMENT OF NF1- OR RAS-ASSOCIATED DISORDERS

(71) Applicant: The Trustees of Dartmouth College, Hanover, NH (US)

(72) Inventors: Yolanda Sanchez, Orford, NH (US); Robert J. Allaway, Norwich, VT (US); Matthew Wood, San Francisco, CA (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/084,129

(22) Filed: Mar. 29, 2016

(65) Prior Publication Data
US 2016/0287562 A1  Oct. 6, 2016

Related U.S. Application Data

(60) Provisional application No. 62/140,007, filed on Mar. 30, 2015.

(51) Int. Cl.
*A61K 31/423* (2006.01)

(52) U.S. Cl.
CPC .................................. *A61K 31/423* (2013.01)

(58) Field of Classification Search
CPC .................................................... A61K 31/423
See application file for complete search history.

(56) References Cited

U.S. PATENT DOCUMENTS

2004/0028660 A1\* 2/2004 Hariri .................... A61K 31/00
424/93.7
2005/0143433 A1\* 6/2005 Singh .................. C07D 261/20
514/379

OTHER PUBLICATIONS

Schafer et al. Drug Discovery Today, 2008, 13 (21/22), 913-916.\*
Horig et al. Journal of Translational Medicine 2004, 2(44), p. 1-8.\*
Daginakatte et al., "Increased c-Jun-NH2-Kinase Signaling in Neurofibromatosis-1 Heterozygous Microglia Drives Microglia Activation and Promotes Optic Glioma Proliferation", Cancer Res 2008, vol. 68(24), Dec. 15, 2008, pp. 10358-10366.
Rodriguez-Enriquez et al., "Tracker Dyes to Probe Mitochondrial Autophagy (Mitophagy) in Rat Hepatocytes", available at http://www.tandfonline.com/loi/kaup20, Autophagy, 2006, vol. 2(1), pp. 39-46.
International Search Report and Written Opinion dated Jun. 27, 2016 for International Patent Application No. PCT/US2016/024734.

\* cited by examiner

*Primary Examiner* — Yong Chu
(74) *Attorney, Agent, or Firm* — Lathrop Gage LLP

(57) ABSTRACT

Isoxazoloanthrones and a method for treating disorders associated or caused by Ras deregulation or dysregulation, for example, disorders associated with alterations in the neurofibromin 1 gene such as Neurofibromatosis Type 1, and proliferative disorders such as glioblastoma are provided.

11 Claims, 14 Drawing Sheets

A.

B.

A.

B.

C.

METHOD FOR THE TREATMENT OF NF1- OR RAS-ASSOCIATED DISORDERS

CROSS-REFERENCE TO RELATED APPLICATIONS

The present application claims the benefit of priority from U.S. Provisional Application Ser. No. 62/140,007 filed Mar. 30, 2015, which is incorporated herein by reference in its entirety.

INTRODUCTION

This invention was made with government support under contract numbers R21 NS060940 awarded by the National Institute of Neurological Disorders and Stroke. The government has certain rights in the invention.

BACKGROUND

Neurofibromatosis Type 1 is a common genetic disorder in humans, occurring in 1 in 2,500-3,500 live births. Neurofibromatosis Type 1 is caused by inherited or de novo mutation in the Neurofibromin 1 (NF1) tumor suppressor gene, which encodes a GTPase activating protein (GAP) for Ras (rat sarcoma viral oncogene homolog) signaling proteins. Neurofibromatosis Type 1 has a broad clinical spectrum, wherein affected individuals can develop benign nervous system tumors called neurofibromas, low-grade astrocytomas, pheochromocytoma, and juvenile myelomonocytic leukemia (Korf (2000) *Oncologist* 5:477-85). Plexiform neurofibromas occurring in deep nerves can degenerate into malignant peripheral nerve sheath tumors (MPNST), a life-threatening consequence of Neurofibromatosis Type 1 (Carroll & Ratner (2008) *Glia* 56:1589-605; Ferner & Gutmann (2002) *Cancer Res.* 62:1573-7). The lifetime risk of MPNST in Neurofibromatosis Type 1 patients is estimated to be 8% to 15%, and the 5-year survival is approximately 20% (Evans, et al. (2002) *J. Med. Genet.* 39:311-4; McGaughran, et al. (1999) *J. Med. Genet.* 36:197-203; Porter, et al. (2009) *Sarcoma* 2009:756395).

Plexiform neurofibromas are heterogeneous, composed of fibroblasts, perineurial cells, mast cells, and Schwann cells, but only Schwann cells have biallelic inactivation of NF1 (Rutkowski, et al. (2000) *Hum. Mol. Genet.* 9:1059-66). In mouse models, targeted deletion of NF1 from the Schwann cell lineage gives rise to neurofibromas (Zhu, et al. (2002) *Science* 296:920-2; Wu, et al. (2008) *Cancer Cell* 13:105-16; Zheng, et al. (2008) *Cancer Cell* 13:117-28). Thus, loss of NF1 from Schwann cell precursors is thought to initiate plexiform neurofibroma. Aberrant signaling occurs between NF1-deficient Schwann cells and NF1 heterozygous mast cells, which generates a tumorigenic microenvironment (Zhu, et al. (2002) *Science* 296:920-2; Yang, et al. (2008) *Cell* 135:437-48; Monk, et al. (2007) *Neuron Glia Biol.* 3:233-44). Because of their role in the initiation of plexiform neurofibroma and progression to MPNST, NF1-deficient Schwann cells represent an ideal population for targeted molecular therapies.

Chemical screens have revolutionized the discovery process for targeted molecular therapies. However, primary Schwann cells are difficult to culture and present a challenge for high-throughput screening. Another challenge in drug discovery is the rapid and efficient identification of the receptor for a novel compound—either the physical ligand or the biological process that is being modified. Approaches addressing these challenges are needed to identify new compounds and target pathways for the devastating tumors that afflict Neurofibromatosis Type 1 patients.

The budding yeast *Saccharomyces cerevisiae* has two NF1 homologues, IRA1 and IRA2, which encode Ras-GAPs (Tanaka, et al. (1990) *Cell* 60:803-7). Deletion of an IRA gene increases Ras-GTP and activates two pathways, a mitogen-activated protein kinase pathway that modifies cell morphology and the cyclic AMP dependent protein kinase (PKA) pathway (Mosch, et al. (1996) *Proc. Natl. Acad. Sci. USA* 93:5352-6; Toda, et al. (1985) *Cell* 40:27-36). Schwann cells lacking NF1 have increased intracellular cyclic AMP and display PKA-dependent phenotypes (Kim, et al. (2001) *J. Neurosci.* 21:1110-6; Xu, et al. (2002) *J. Neurosci.* 22:9194-202). The fact that Schwann cells lacking NF1 and budding yeast lacking IRA2 share the high PKA phenotype indicates that the yeast model is useful for targeting the cell-autonomous effects of NF1 loss in Schwann cells. The yeast platform enables rapid and cost effective high-throughput chemical screening and allows for the use of powerful yeast genetics to identify new drug targets.

In this respect, high-throughput chemical screens in mammalian MPNST cell lines and in yeast have been carried out to identify therapeutic agents and target pathways for Neurofibromatosis Type 1-associated tumors. See Wood, et al. (2011) *Mol. Cancer Ther.* 10:1740, US 2012/0302581, US 2013/0345268, and US 2010/0209931.

Isoxazoloanthrones are a class of compounds which have been described for use in treating HCV infection (see US 2005/09143433) and for inhibiting Jun N-terminal Kinase (JNK) and treating or preventing a disease associated with modulation of JNK (see U.S. Pat. No. 7,354,947).

SUMMARY OF THE INVENTION

In one aspect, provided herein is a method for treating a disorder associated with Ras deregulation or dysregulation by administering to a subject in need of treatment an effective amount of a compound having the structure of Formula I, or a hydrate, isomer, prodrug or pharmaceutically acceptable salt thereof:

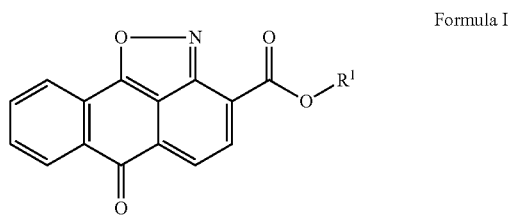

Formula I wherein $R^1$ is a branched or straight chain, saturated or unsaturated, alkyl radical with 1 to 18 carbon atoms. In certain embodiments, $R_1$ is a branched or straight chain alkyl radical with 1 to 6 carbon atoms.

In one embodiment, the compound of Formula I is selected from the group consisting of:

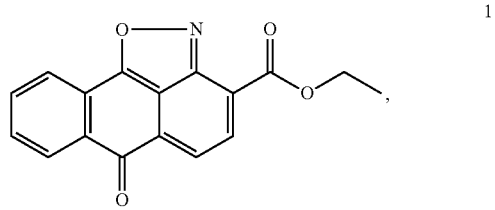 [SMILES: CCOC(=O)c1ccc2c3c(onc13)-c1ccccc1C2=O]

1

-continued

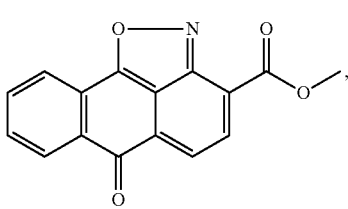
2 and pharmaceutically acceptable salts thereof.

In a particular embodiment, the compound of Formula I is:

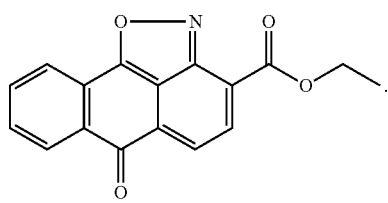
1

In another particular embodiment, the compound of Formula I is

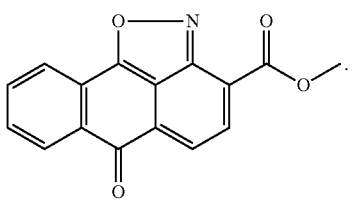
2

In some embodiments, the disorder associated with Ras deregulation or dysregulation is a disease state that results from a mutation or loss of function in a neurofibromin 1 gene, e.g., Neurofibromatosis Type 1. In other embodiments, the disorder associated with Ras deregulation or dysregulation is neuroblastoma, lung adenocarcinoma, squamous cell carcinoma, glioblastoma, pancreatic cancer, ovarian cancer, colon cancer, lung cancer, neurofibromas, malignant peripheral nerve sheath tumor, optic glioma, Schwannoma, glioma, leukemia, pheochromocytoma or pancreatic adenocarcinoma.

In a particular embodiment, provided herein is a method of treating Neurofibromatosis Type 1 comprising administering to a subject in need of such treatment an effective amount of the compound:

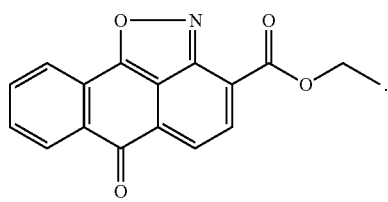
1

In another particular embodiment, provided herein is a method of treating Neurofibromatosis Type 1 comprising administering to a subject in need of such treatment an effective amount of the compound:

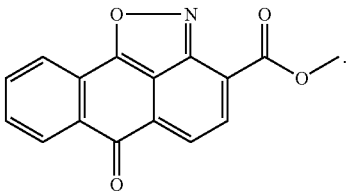
2

In another aspect, provided herein is a method of inhibiting autophagy in a cell, comprising contacting the cell with a compound of the invention according to an embodiment described herein.

In another aspect, provided herein is the use of a a compound of the invention according to an embodiment described herein, in a method for treating a disorder associated with Ras deregulation or dysregulation.

DETAILED DESCRIPTION OF THE INVENTION

Figure 1:
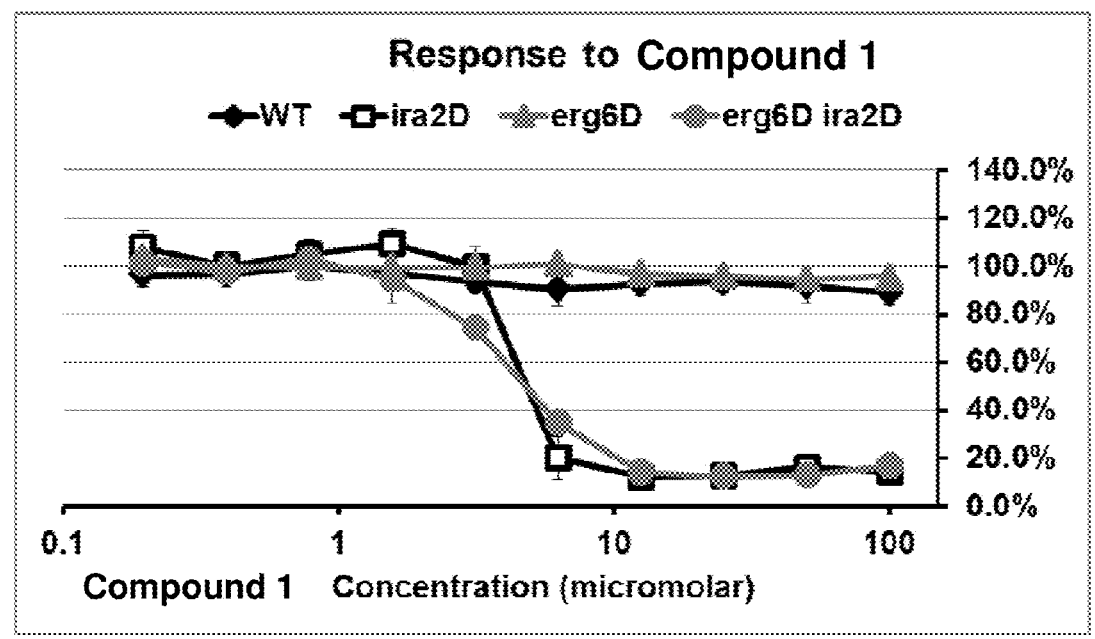
FIG. 1 shows that compound 1 selectively inhibits growth or induces cell death in a yeast model of NF1 deficiency without affecting the control strains. IRA2 is a yeast homolog of human NF1. Cells were grown in the presence of increasing concentrations of compound 1 for 18 hours. The absorbance (OD 600 nm) was measured as a surrogate marker of cell growth. The assay has been described previously: see Sanchez et al., Mol. Cancer Ther. 2011 Sep.: 10(9):1740-1750.
Figure 2:
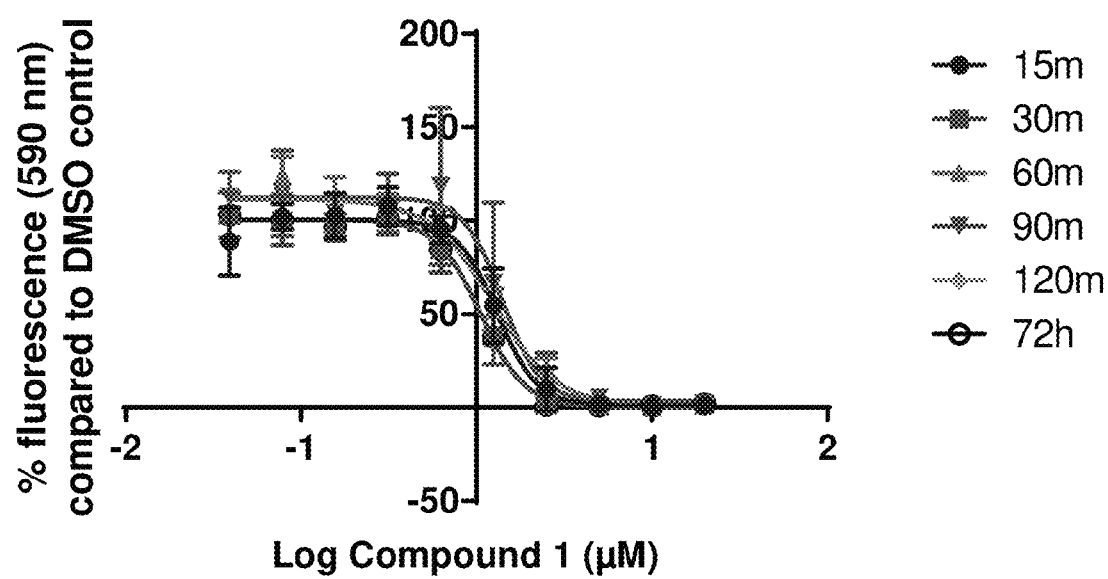
FIG. 2 shows that compound 1 has an irreversible effect on cell viability/growth of NF1-deficient tumor cells (U87-MG) within 15 minutes. Cells were incubated with drug for 15 minutes-72 h. At the noted times, the drug was removed, cells were rinsed with PBS, and replaced with normal media. At 69 hours, 5 uL of alamarBlue viability assay reagent was added to each well. At 72 h, the fluorescence was measured (Ex/Em 544/590 nm) as a surrogate indicator of viability. All values were normalized to the fluorescence observed in a vehicle (DMSO) control.
Figure 3:
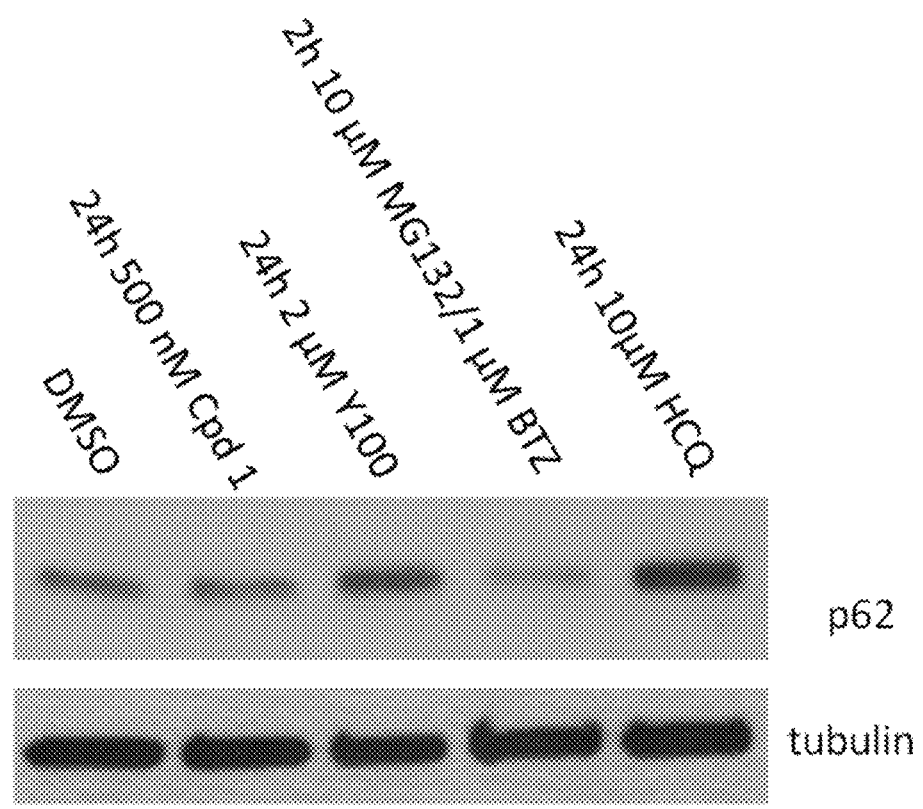
FIG. 3 shows that compound 1 modulates the autophagy marker and ubiquitin binding scaffold protein p62/SQSTM-1. U87-MG tumor cells were treated with compound 1 or hydroxychloroquine (an autophagy inhibitor) for 24 h or a cocktail of proteasome inhibitors (bortezomib, BTZ and MG-132) for 2 h. P62 and tubulin levels were determined by western blot.
Figure 4:
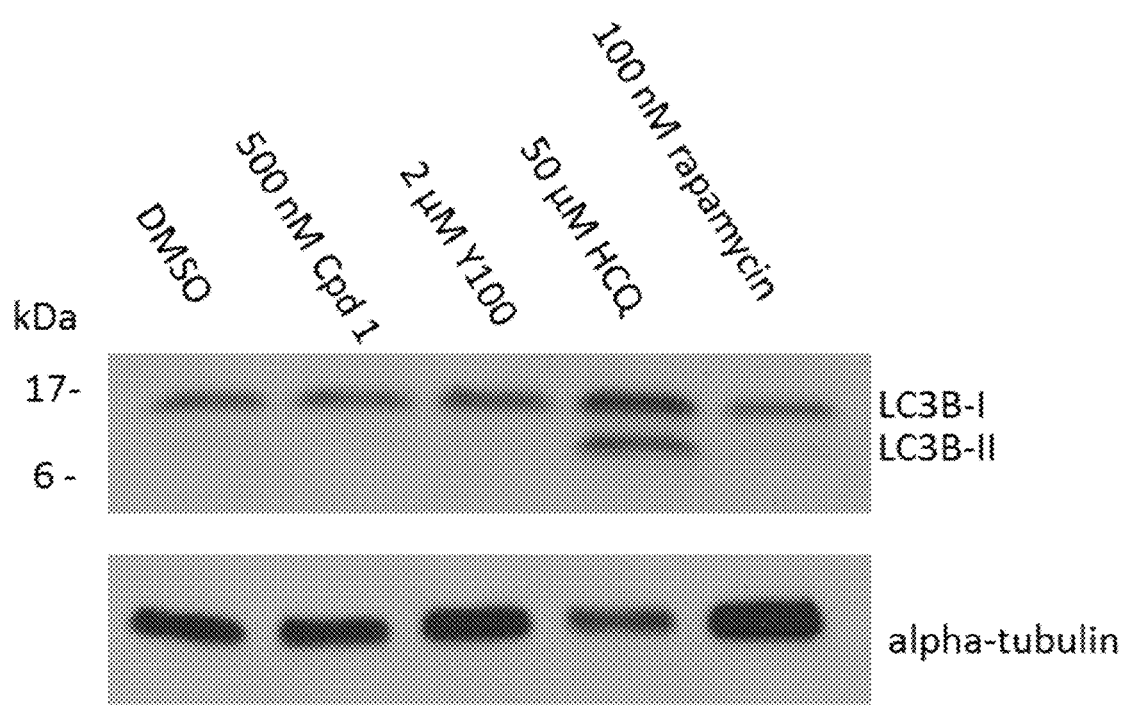
FIG. 4 shows that compound 1 modulates autophagy by a different mechanism than hydroxychloroquine, which induces accumulation of the autophagy marker LC3B-II. U87-MG tumor cells were treated with Y100, hydroxychloroquine (an autophagy inhibitor) or rapamycin (an autophagy inducer) for 24 hours. LC3B-I to LC3-II conversion and tubulin levels were determined by western blot. These data are recapitulated by immunofluorescent microscopy, showing that compound 1 induces P62 accumulation but not LC3B accumulation as indicated by immunofluorescent staining of compound 1 and hydroxychloroquine treated U87-MG cells.
Figure 5:
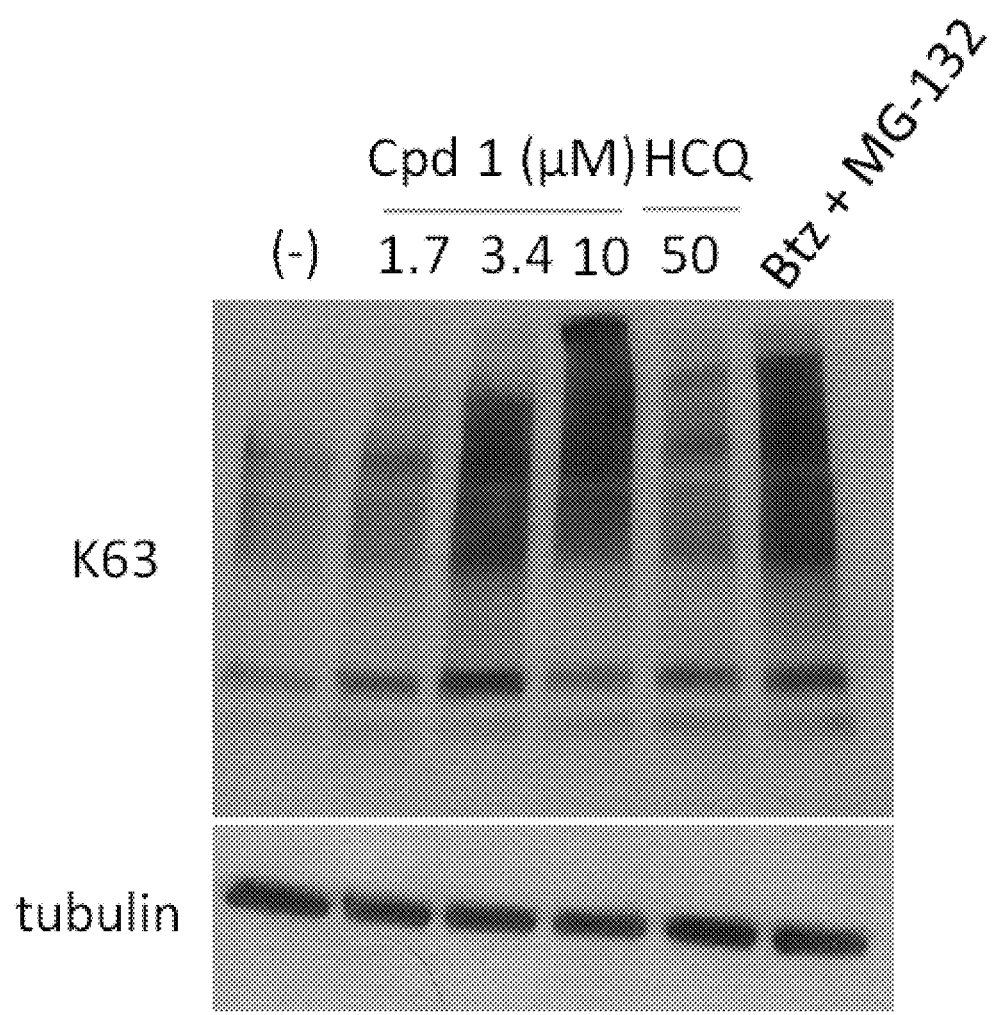
FIG. 5: (A) and (B) show that treatment with compound 1 for 24 hours induces the accumulation of lysine 63 and lysine 48 polyubiquitin linked-proteins in U87-MG and U251-MG cells. The accumulation is comparable to treatment with the autophagy inhibitor HCQ (hydroxychloroquine) (50 uM, 24 h) or a cocktail of proteasome inhibitors, MG132 (2 h, 10 micromolar) and bortezomib (Btz, 2 h, 1 micromolar).
Figure 5:
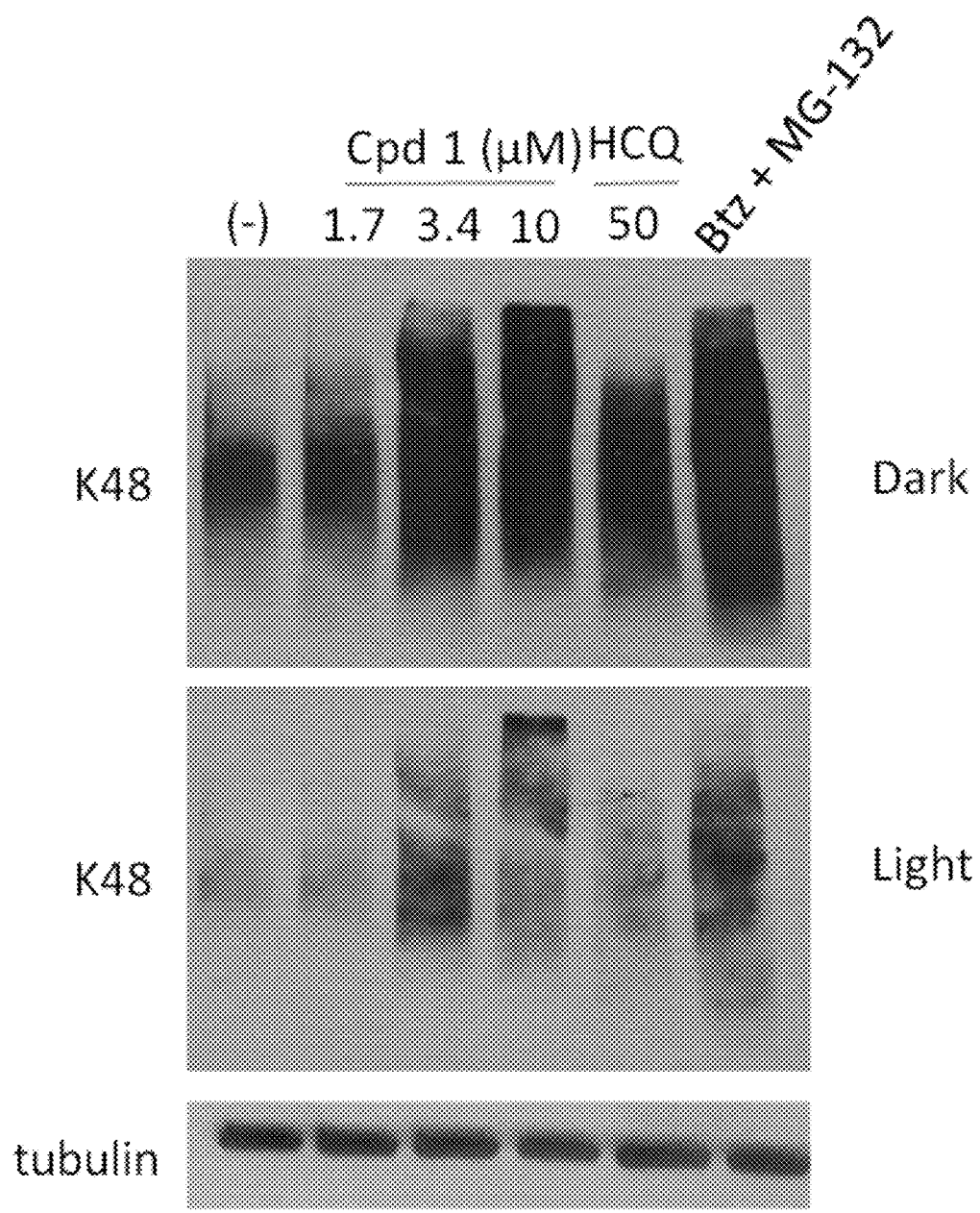
Figure 6:
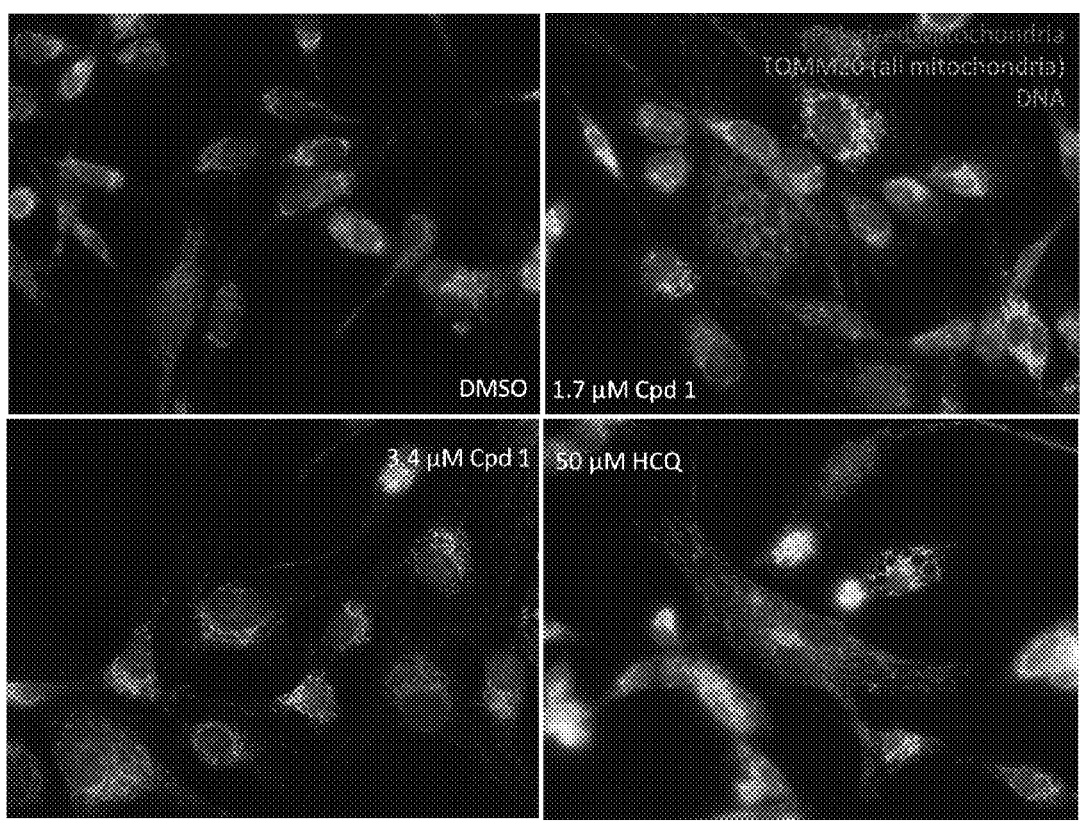
FIG. 6 shows that compound 1 induces the formation of polarized mitochondrial hotspots in U87-MG and U251-MG cells. Polarized mitochondria are labeled with Mitotracker Red, while all mitochondria are labeled with an antibody specific to the mitochondrial protein TOMM20.
Figure 7:
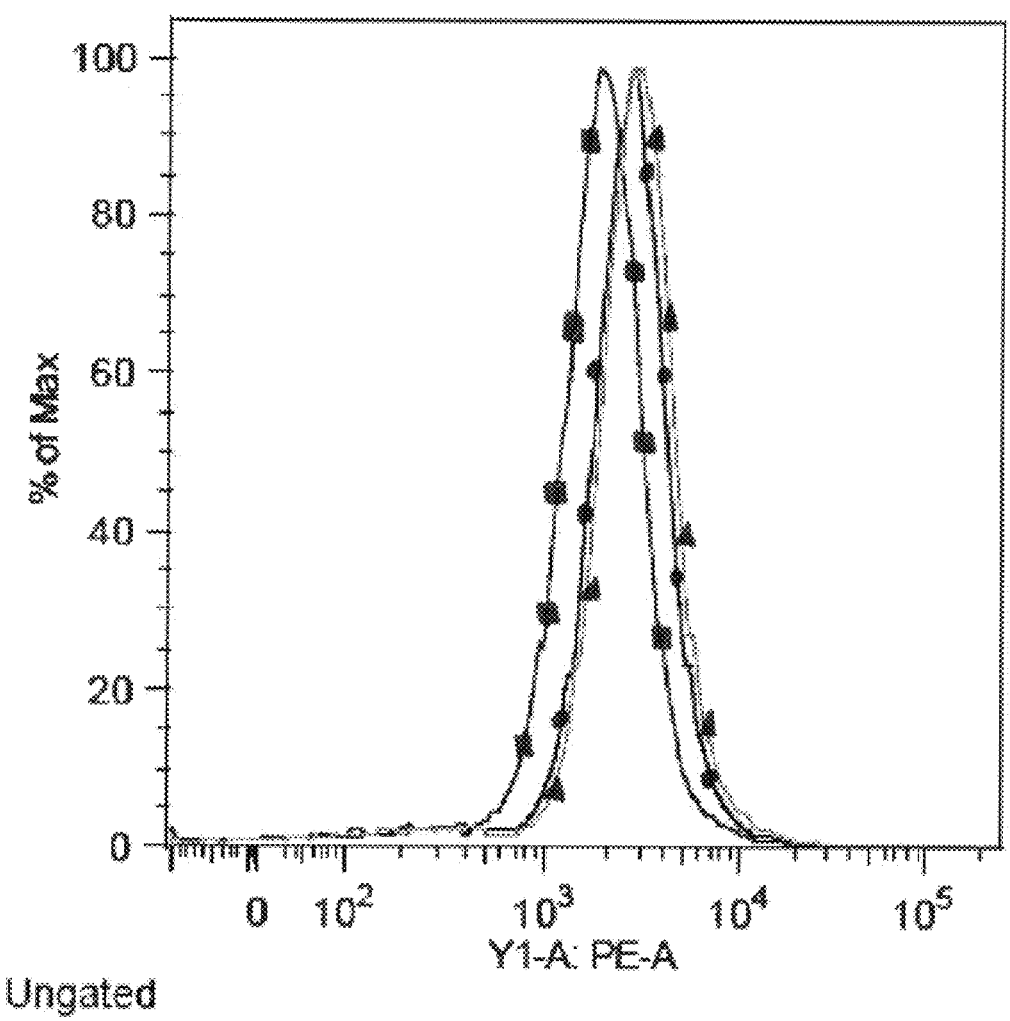
FIG. 7 shows that 24 h of treatment with compound 1 induces the formation and/or accumulation of mitochondrial superoxide as indicated by flow cytometry with the reagent MitoSOX Red, a marker for superoxide originating in the mitochondria.
Figure 8:
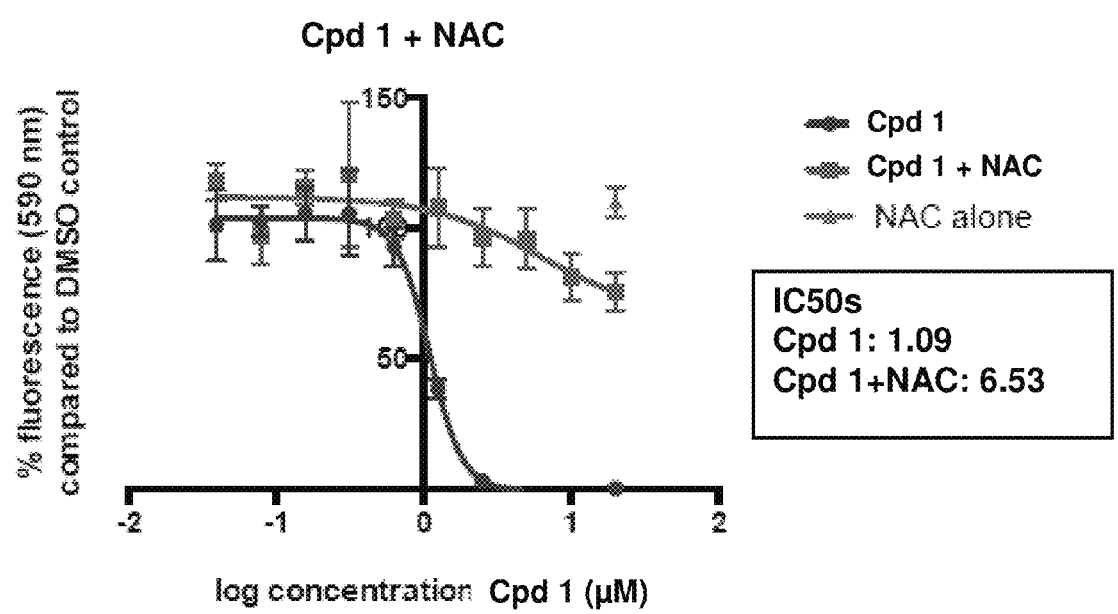
FIG. 8: (A), (B) and (C) show that the ROS (reactive oxygen species) scavengers N-acetyl cysteine (NAC) and β-mercaptoethanol abrogate the effect of compound 1 on U87-MG cells when co-treated for 72 hours, as indicated by an alamarBlue assay. Pretreatment and co-treatment of U87-MG cells with the glutathione synthesis inhibitor buthionine sulfoximine (BSO) potentiates the effect of compound 1 on cell viability/growth in a 3-day alamarBlue assay.
Figure 8:
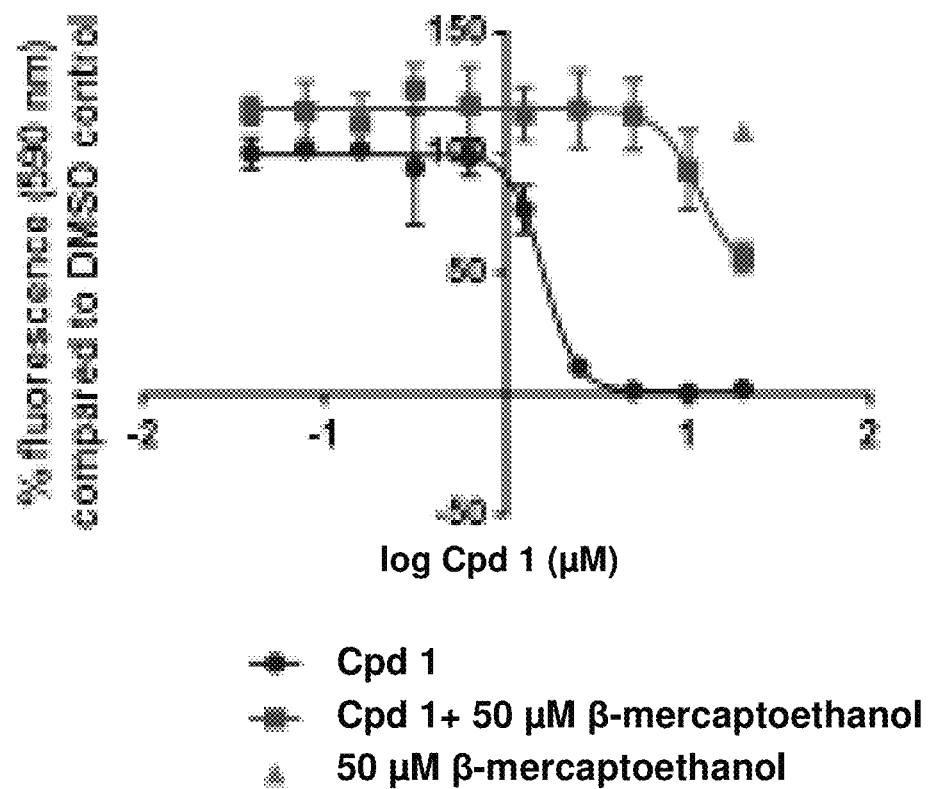
Figure 8:
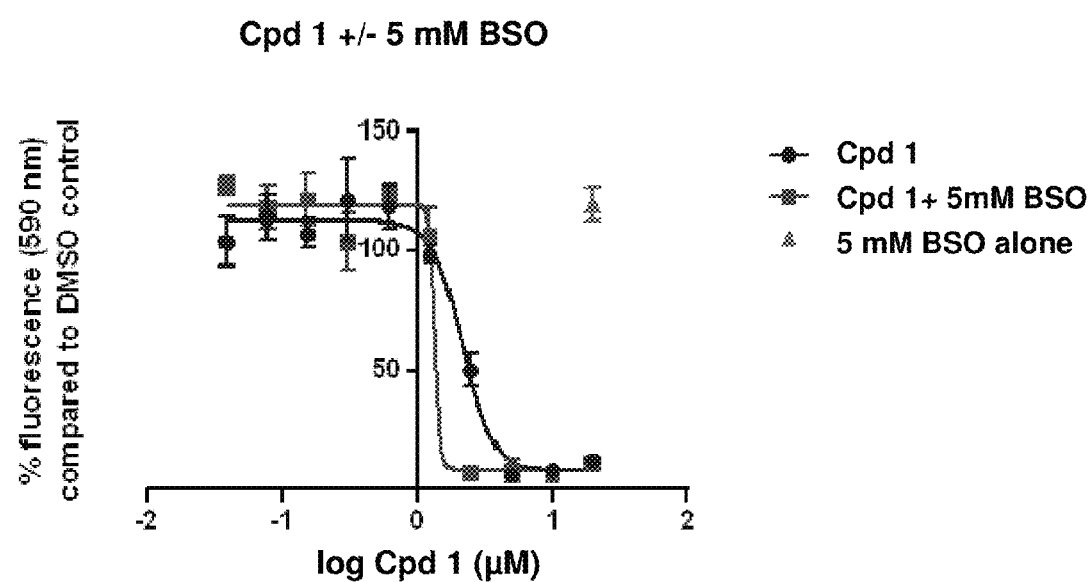
Figure 9:
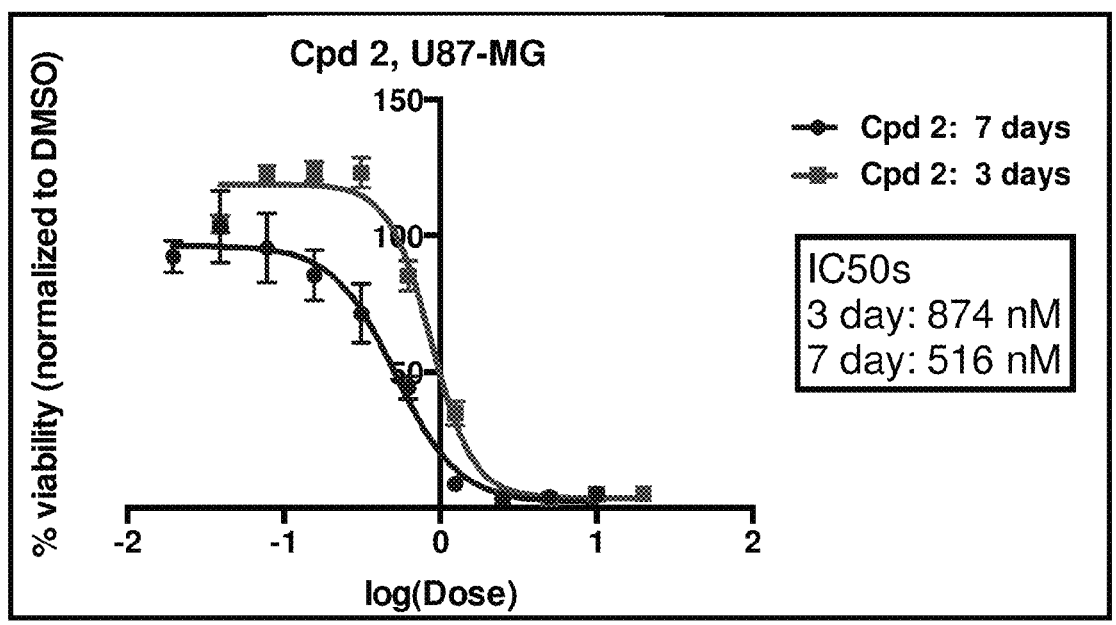
FIG. 9 shows that compound 2 reduces viability and/or growth of NF1-deficient U87 MG cells. Cells were incubated with drug for 3 or 7 days. 3 hours before the end of the experiment, 5 uL of alamarBlue viability assay reagent was added to each well. At the end of each timepoint, the fluorescence was measured (Ex/Em 544/590 nm) as a surrogate indicator of viability. All values were normalized to the fluorescence observed in a vehicle (DMSO) control.
Figure 10:
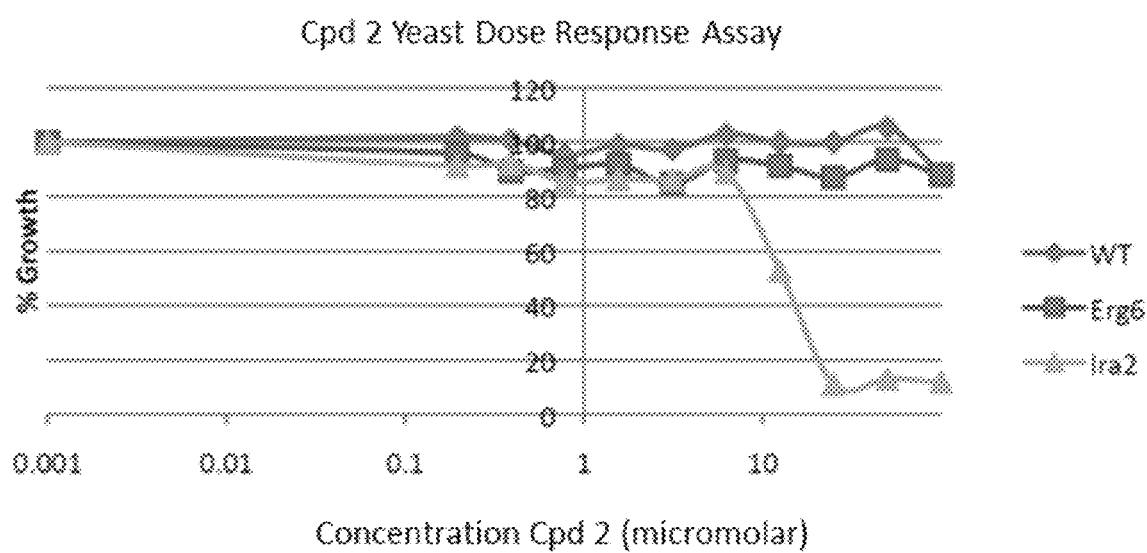
FIG. 10 shows that compound 2 selectively inhibits growth or induces cell death in a yeast model of NF1 deficiency without affecting the control strains. IRA2 is a yeast homolog of human NF1. Cells were grown in the presence of increasing concentrations of Y100B for 18 hours. The absorbance (OD 600 nm) was measured as a surrogate marker of cell growth. The assay has been described previously: see Sanchez et al., Mol. Cancer Ther. 2011 Sep.: 10(9):1740-1750.

A class of isoxazoloanthrones have now been identified that inhibit the growth and/or viability of NF1-deficient yeast, as well as NF1 and/or Ras dysregulated mammalian tumor cells, including glioblastoma multiforme, neuroblastoma, malignant peripheral nerve sheath tumors, pancreatic ductal adenocarcinoma, and lung adenocarcinoma. In yeast, it was observed that the following genes may be components of the pathway targeted by these compounds: VTC4, VAC14, IRS4, ATG23, ATG38, SSK1, UNG1, MRPS5, PCP1, GTF1, RMA1, CIT1, PDH1, ICL2, YDR514C and COS111 among others. In human tumor cells, it was observed that these compounds modulate autophagy as indicated by accumulation of the autophagy marker P62. The mechanism of action appears to be distinct from that of the classic autophagy inhibitor hydroxychloroquine, which induces P62 accumulation, as well as LC3B-II accumulation. However, these compounds do not appear to induce apoptotic or necroptotic cell death. Proteasome target genes such as cyclin E and HIF-1α are modulated by the compounds of this invention; however, K63 and K48-linked polyubiquitin tagged proteins accumulate in the presence of the compounds, thereby suggesting that the proteasome is inhibited by another mechanism, or a subtype of autophagy such as mitophagy. Moreover, an MV-151 fluorescent probe assay indicates that compounds of the invention are not direct inhibitors of the proteasome. Compounds of the invention induce dysregulation of mitochondrial dynamics as treatment with said compounds induces punctate morphology of polarized mitochondria (mitochondrial hotspots). Based on these results, the present invention provides compounds for use in a method for treating disorders associated with deregulation or dysregulation of Ras and/or for the treatment and/or prevention of Neurofibromatosis Type 1 or NF1-related disorders or conditions.

The isoxazoloanthrone compounds of use in the method disclosed herein have the structure of Formula I, which includes hydrates, isomers, prodrugs or pharmaceutically acceptable salts of Formula I:

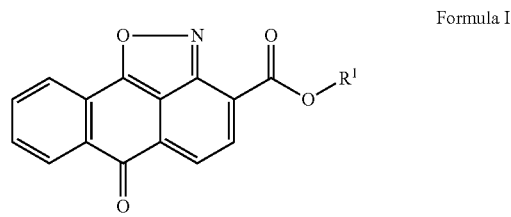

Formula I wherein $R^1$ is a branched or straight chain, saturated or unsaturated, alkyl radical with 1 to 18 carbon atoms (i.e., $C_1$-$C_{18}$). Examples of "alkyl" as used herein include methyl, ethyl, propyl, isopropyl, n-butyl, isopentyl, n-pentyl, hexyl, heptyl, octyl, nonyl, decyl groups and the like, as well as substituted versions thereof. In particular embodiments, an alkyl of the invention is a branched or straight chain alkyl radical with 1 to 6 carbon atoms.

Unless otherwise specifically stated, use of the term "substituted" or "substituent" means any group or atom other than hydrogen. Additionally, when a group, compound or formula containing a substitutable hydrogen is referred to or when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for activity. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, and cyclohexyl; alkenyl, such as ethylene, 2-butene; alkoxy, such as methoxy, ethoxy, propoxy, butoxy, 2-methoxyethoxy, sec-butoxy, and hexyloxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, phenylcarbonylamino, p-tolylcarbonylamino, N-methylureido, NN-dimethylureido, N-phenylureido, and N,N-diphenylureido; sulfonamido, such as methylsulfonamido, benzenesulfonamido, p-tolylsulfonamido, and N,N-dipropyl-sulfamoylamino; sulfamoyl, such as N-methylsulfamoyl, N-ethylsulfamoyl, N,N-dipropylsulfamoyl, and N-phenylsulfamoyl; carbamoyl, such as N-methylcarbamoyl, N,N-dibutylcarbamoyl, N-benzylcarbamoyl; acyl, such as acetyl, propanoyl, benzoyl and 4-methyl benzoyl; oxyacyl, such as phenoxycarbonyl, methoxycarbonyl, butoxycarbonyl, ethoxycarbonyl, and benzyloxycarbonyl; sulfonyl, such as methylsulfonyl, ethylsulfonyl, phenylsulfonyl, 4-fluorophenylsulfonyl, phenoxysulfonyl, and p-tolylsulfonyl; sulfinyl, such as methylsulfinyl, ethylsulfinyl, phenylsulfinyl, and p-tolylsulfinyl; thio, such as methylthio, ethylthio, benzylthio, phenylthio, and p-tolylthio; acyloxy, such as acetyloxy, and benzoyloxy; amine, such as anilino, 2-chloroanilino, dimethylamine, methylamine; a heterocyclic group, a heterocyclic oxy group or a heterocyclic thio group, each of which may be substituted and which contain a 5 to 7 membered heterocyclic ring composed of carbon atoms and at least one hetero atom selected from the group consisting of oxygen, nitrogen, or sulfur, such as 2-furyl, 2-imidazolyl, 4-imidazolyl, 2-thienyl, 2-benzimidazolyloxy or 2-benzothiazolyl. If desired, the substituents may themselves be further substituted one or more times with the described substituent groups. The particular substituents used may be selected by those skilled in the art to attain desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Exemplary compounds of the invention and associated NCBI PubChem CIDs include, but are not limited to:

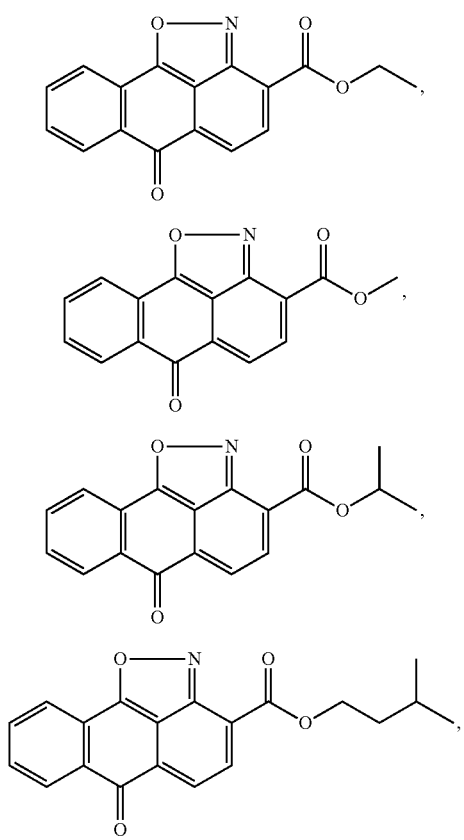

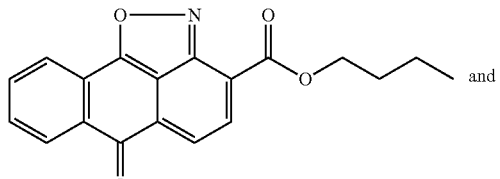

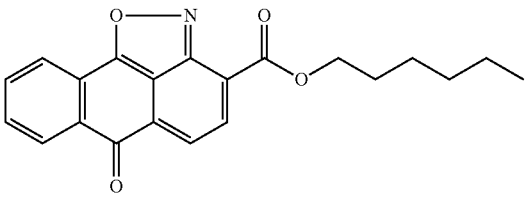

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl) benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some embodiments of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy or carboxy group is bonded to any group that, when the prodrug is administered to a patient, cleaves to form a hydroxy or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexyl-sulfamates, quinates, esters of amino acids, and the like.

Compounds of the invention can be prepared using any suitable methodology routinely practiced in the art (see, e.g., US 2005/09143433 and U.S. Pat. No. 7,354,947), and be analyzed for their pharmacological properties by routine methodologies. For example, kinetic solubility can be measured using a direct UV absorbance method or thermodynamic solubility can be measured. In addition, stability in gastrointestinal fluids can be determined by conventional methods (Asafu-Adjaye, et al. (2007) *J. Pharm. Biomed. Anal.* 43:1854-1859), e.g., 1 hour in simulated gastric fluid (pH 1.2, pepsin) at 37° C. and/or 3 hours in simulated intestinal fluid (pH 6.8, pancreatin). Furthermore, using the Parallel Artificial Membrane Permeability Assay (PAMPA)-blood-brain barrier (BBB) permeability assay (Di, et al. (2009) *J. Pharm. Sci.* 98:1980-1991) or B-P dialysis (Kalvass & Maurer (2002) *Biopharm. Drug Dispos.* 23(8):327-38), brain penetration can be assessed. Furthermore, lipophilicity can be estimated by partitioning between octanol and water using a shake flask method or pH metric method and permeability can be assessed using the Caco-2 cell layer method of PAMPA assay.

A compound of this invention may be administered in a pharmaceutical composition by various routes including, but not limited to, intradermal, intramuscular, intraperitoneal (e.g., by injection), intravenous, subcutaneous, intranasal, epidural, oral, sublingual, intracerebral, transdermal, rectal, intratumoral or topical administration. Depending on the route of administration, the active compound may be coated. For example, to administer the therapeutic compound by a route other than parenteral administration, it may be necessary to coat the compound with, or co-administer the compound with, a material to prevent its inactivation. By way of illustration, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) J. Neuroimmunol. 7:27). Further, to facilitate delivery, decrease toxicity and/or increase solubility, a compound of the invention can be combined with a carrier such as cyclodextrin, castor oil, Cremaphor™ EL or a nanoparticle packaging system.

When the compound is to be administered parenterally, intraperitoneally, intraspinally, or intracerebrally, dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Compounds of Formula I can be used alone or in combination with one or more other therapeutics, in particular anticancer agents. Such anticancer agents can include DNA damaging agents, DNA synthesis inhibitors, mitosis inhibitors, cell division inhibitors, antiangiogenic agents, hormonal derivatives, alkylating agents, antimetabolites, antiproliferative agents, plant alkaloids, topoisomerase inhibitors or antitumor agents. As used herein, administration "in combination with" one or more anticancer agents includes simultaneous (concurrent) and consecutive administration in any order. According to the method of the invention, a composition containing a compound of Formula I may be administered prior to, concurrent with, or following an anticancer agent(s). The administration schedule may involve administering the different compounds in an alternating fashion and/or in different administration regimes. In other embodiments, the anticancer agent may be delivered before and during, or during and after, or before and after treatment with a compound of Formula I.

Having demonstrated that the isoxazoloanthrones of the invention can inhibit the growth and/or viability of NF1-deficient yeast, as well as NF1 and/or Ras dysregulated mammalian tumor cells, the present invention provides compositions containing one or more compounds of the invention and use thereof in a method for treating a disorder associated with Ras deregulation or dysregulation and/or a NF1-related disorder or condition.

Deregulation of the protein "Ras" is associated with a wide range of disease states. There are several Ras isoforms in humans. The predominant isoforms believed to be relevant to human cancer are K-Ras (NCBI Accession Number NG_007524) (having two splice variants), H-Ras (NCBI Accession Number NG_007666), and N-Ras (NCBI Accession Number NG_007572). The mammalian R-Ras is most similar to S. cerevisiae Ras1 and Ras 2. Frequently, tumors acquire mutations in one of these genes that render the protein constitutively active (deregulated). In other disease states, upstream effector molecules may lose function or otherwise be affected such that Ras is deregulated. For example, the Ras signaling pathway may be activated by amplification of certain growth factor receptors, or by activating mutations in growth factor receptor genes. Several other inherited syndromes are associated with deregulated Ras signaling (Ras-opathies), for example Neurofibromatosis Type 1, Costello syndrome, Noonan syndrome, and LEOPARD syndrome. These disorders may be caused by deregulation of the Ras signaling pathway, predominantly by activating mutations in K-Ras and H-Ras or loss of upstream regulators.

Thus, with reference to the method herein, the term "deregulated" or "deregulation" means that the regulation of a gene or protein has been removed such that the level or activity of the gene product is altered or modified. The term "dysregulated" or "dysregulation" refers to a dysfunctional level or activity of a gene product, which has detrimental consequences.

The phrase "disorder associated with Ras deregulation or dysregulation" includes diseases wherein the etiology of the disorder involves deregulation/dysregulation of RAS signaling, for example, wherein RAS activity may be increased to the extent that a disease state arises. The Ras forms contemplated herein encompass any known variant of Ras and include K-Ras (e.g., NCBI Accession Number NG_007524) (having two splice variants), H-Ras (e.g., NCBI Accession Number NG_007666), and N-Ras (e.g., NCBI Accession Number NG_007572), and R-Ras (e.g., NCBI Accession Number NC_000019 (Gene ID 6237)), Ras 1, Ras 2 and combinations thereof. The disorder associated with Ras deregulation or dysregulation may be a proliferative disorder such as cancer. The disorder associated with Ras deregulation or dysregulation may be Neurofibromatosis Type 1, a disease state that results from a mutation or loss of function in the NF1 gene (NCBI Accession Number NG_009018), neuroblastoma, lung adenocarcinoma, squamous cell carcinoma, glioblastomas (e.g., glioblastoma multiforme), ovarian cancer, colon cancer, lung cancer, including lung adenocarcinoma, neurofibromas, malignant peripheral nerve sheath tumors, optic gliomas, Schwannomas, gliomas, leukemias, pheochromocytomas, pancreatic cancer, pancreatic adenocarcinoma (wherein greater than about 90% of tumors have activating mutations in K-Ras), including pancreatic ductal adenocarcinoma and/or other sporadic cancers, and may also include non-tumor manifestations such as learning disorders and/or fungal infections such as those involving the transformation of fungi to the invasive hyphal form, e.g., as in Candida albicans infections.

The NF1 protein is a GTPase-activating ("GAP") protein for Ras proteins. The NF1 gene locus represents a mutational hotspot. Loss of NF1 results in increased levels of Ras-GTP. NF1 mutation in MPNST cells also leads to increased MAP kinase and PKA activation. Loss of function mutations in the NF1 gene results in an autosomal dominant disorder known as Neurofibromatosis Type 1 that affects 1 in 2,500 to 3,500 live births. It is believed that activated Ras can lead to many of the phenotypes observed in Neurofibromatosis Type 1 patients, such as uncontrolled proliferation and aberrant migration of Schwann cells. 95% of patients will develop neurofibromas that associate with nerve endings (dermal) or large nerves (plexiform). 30% of patients develop plexiform neurofibromas that can cause disfigurement and/or compression of organs, which can have devastating consequences. Furthermore, 8-13% of patients will develop malignant peripheral nerve sheath tumors ("MPNST"s), the most severe manifestation of Neurofibromatosis Type 1 disease. These tumors are aggressive soft tissue sarcomas with poor prognosis. Half of all MPNSTs are sporadic in nature; half arise in individuals with loss of function mutations in the NF1 gene. MPNSTs represent a major cause of mortality in NF1 patients.

Thus, the phrase "NF1-related disorder or condition" means any disease state or disorder or symptoms that result from, or is associated with, a mutation, deletion, dysregulation or other alteration of the NF1 gene. Such disorders include Neurofibromatosis Type 1. Associated conditions include neurofibromas, malignant peripheral nerve sheath tumors, optic gliomas, Schwannomas, gliomas, leukemias, pheochromocytomas and non-tumor manifestations, including learning disorders.

The method of this invention involves the step of administering to a subject in need of treatment, e.g., a mammal (preferably a human) a prophylactically or therapeutically effective amount of one or more compound of Formula I. Subjects in need of treatment include those having, suspected of having, or at risk of having a disorder or condition associated with Ras deregulation or dysregulation and/or a NF1-related disorder or condition. A subject having or suspected of having a disorder or condition is one exhibiting one or more signs or symptoms associated with the disorder or condition. A subject at risk of having a disorder or condition includes, e.g., subjects having a mutation associated with the disorder or condition, but not showing signs or symptoms of the disorder or condition.

A prophylactically effective amount denotes the amount of a compound of the invention that is of sufficient quantity to prevent, delay onset, or reduce the risk of developing a disorder or condition described herein. A therapeutically effective amount refers to the amount of a therapy sufficient to result in (i) the amelioration of one or more symptoms of a disorder, (ii) prevent advancement of a disorder, (iii) cause regression of a disorder, or (iv) to enhance or improve the therapeutic effect(s) of another therapy (e.g., an anticancer agent). The amount of the subject compound is generally sufficient to significantly induce a positive modification in the condition to be treated, but low enough to avoid serious side effects (at a reasonable benefit/risk ratio), within the scope of sound medical judgment. The effective amount of the subject compound will vary with the age and physical condition of the patient being treated, the severity of the condition, the duration of the treatment, the nature of concurrent therapy, the particular pharmaceutically acceptable carrier utilized, and like factors within the knowledge and expertise of the attending physician. Preparing a dosage form is within the purview of the skilled artisan. Examples are provided for the skilled artisan, but are non-limiting, and it is contemplated that the skilled artisan can prepare variations of the compositions claimed.

The following non-limiting examples are provided to further illustrate the present invention.

EXAMPLE 1

Materials and Methods

MPNST Tumor Acquisition and Processing. Tumor specimens and corresponding clinical data are collected and used in accordance with Institutional Review Board-approved protocols. The diagnosis of NF1 is established according to published criteria (NIH Consensus Statement). Frozen, archived tumor specimen pathology is reviewed and RNA isolated and then analyzed on AFFYMETRIX U95AV2 GENECHIP microarray.

Viability Assay. Cells are cultured on plastic 96-well plates. Cell viability is estimated using metabolism as a surrogate marker via the ALAMARBLUE viability/proliferation assay (AbD Serotec; Kidlington, UK) according to the protocol of the manufacturer. The modification of the ALAMARBLUE reagent to a fluorescent substrate is measured with a fluorimeter, after which fluorescent intensity is normalized as a percentage of the vehicle control. Assays are done in triplicate.

Determination of $LD_{50}$. Mice are injected interperitoneally at an initial dose which is that of the $IC_{50}$, increasing in ⅓ Log steps, to determine the lethal dose ($LD_{50}$). The dose at which toxic effects are noted can also be determined to ensure that the "therapeutic" dose is well below the toxic dose. Necropsy can be performed on animals that receive compounds of the invention to evaluate for possible toxic effects on animal organs. Tissues obtained include brain, spinal cord, heart, lungs, spleen, liver, large intestines, muscle, bone, and bone marrow.

Immunofluorescence. U87-MG cells were cultured on poly-D-lysine coated coverslips (Neuvitro Corporation) or poly-L-lysine coated coverslips and treated with Compound 1 (Chembridge) for 24 hours. For the last 30 minutes of treatment, cells were labeled with 100 nM Mitotracker Red (Life Technologies). After treatment and labeling, cells were rinsed with PBS. Cells were fixed in 4% methanol-free paraformaldehyde (Electron Microscopy Services) in PBS (Corning) for 10 minutes at room temperature and blocked with immunofluorescence buffer (2% [v/v] goat serum, 0.2% [v/v] Triton X-100 and 0.05% [w/v] sodium azide in PBS) at RT. TOMM20 was labeled using 1:200 rabbit anti-TOM20 (Santa Cruz) at room temperature for one hour, and cells were rinsed 3 times for 5 minutes with PBST. Secondary labeling was performed with 1:600 goat anti-rabbit F(ab') 2 DyLight 488 at room temperature for 1 hour (Jackson Immunoresearch) diluted in IF buffer. Cells were then rinsed 2 times for five minutes with PBST and then nuclei were labeled with DAPI in PBS for 5 minutes. Coverslips were mounted on glass slides with ProLong Gold (Life Technologies). Images were acquired with a Zeiss Imager Z1 wide-field microscope equipped with a 40×1.3 NA EC Plan-NEOFLUAR objective and Zeiss Axiovision software.

Dose Response Assays (Mammalian Cells). To perform drug sensitivity assays, U87-MG cells were plated to 96-well plates at a concentration of 5000 cells/well. After overnight incubation, medium was removed and replaced with 100 µL of medium containing 0-20 uM Compound 1 and DMSO (to normalize DMSO concentrations). In the case of the beta-mercaptoethanol and N-acetyl cysteine co-treatment assays, cells were preincubated with these compounds or a vehicle control for 2 h before being replaced with Y100+/− N-acetyl cysteine, beta-mercaptoethanol or vehicle. Cells were incubated for the noted time with a final 3-hour incubation in 5% AlamarBlue (Thermo Scientific). The plate was scanned at an Ex/Em of 544/590 nm, and fluorescence was normalized to vehicle control wells. Dose-response curves and $IC_{50}$s were calculated with the Prism 6 software package (GraphPad, San Diego, Calif., USA) by performing a 4-parameter logistic regression with outlier exclusion analysis.

Flow Cytometry. To determine mitochondrial superoxide levels, 500,000 U87-MG cells/well were plated to a 6-well plate and allowed to adhere overnight. The medium was then replaced with cell culture media containing DMSO or Y100. Cells were treated for 24 hours. 30 minutes before the end of the incubation, 1 micromolar MitoSOX Red was added. At the end of the incubation, cells were rinsed with PBS and trypsinized, and then rinsed two more times. The cells were transferred to flow cytometry tubes and analyzed using a MacsQuant VYB 8-color flow cytometer. MitoSOX Red fluorescence was detected using the Y1-A (PE) channel. 30,000 events per sample were collected. Histograms were generated using the FlowJo flow cytometry analysis software package.

Figure 11:
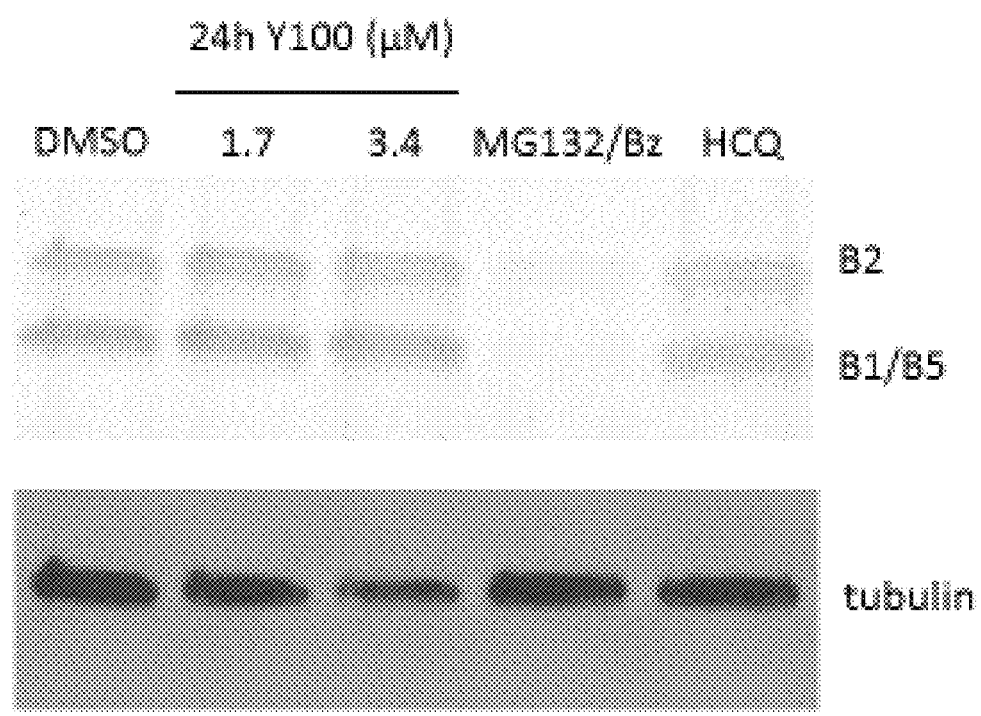
FIG. 11 depicts results of an MV-151 Assay.

MV-151 Assay. U87-MG cells were plated (500,000 cells per well in a 6-well tissue culture plate) and allowed to adhere overnight. Cells were treated for 24 hours with vehicle control (DMSO), Compound 1 (Y100), or a 2 h incubation of a cocktail of bortezomib (Bz) and MG132 (proteasome inhibitors) as a positive control. The cells were lysed with a digitonin-based buffer. Lysates were incubated with a MV151, a fluorescent probe that binds active proteasome subunits, and samples (10 ug total protein per sample) were seperated on an SDS-PAGE gel. The gel was then scanned on a Typhoon scanner to detect MV151 fluorescence, and then protein was transferred to a nitrocellulose membrane and probed for beta-tubulin as a loading control. See FIG. 11.

Western Blotting. U87-MG cells were plated at a concentration of 500,000 cells per well in a 6-well plate and allowed to adhere overnight. Cells were treated with the noted concentrations and times of controls or compound 1. After treatment, cells were harvested with trypsin, rinsed, and lysed with approximately 75 microliters RIPA buffer with protease and phosphatase inhibitors per 500,000 cells. Protein was quantified with a BCA assay kit (Pierce). 30 micrograms of protein was separated on a 4-15% SDS-PAGE gel (Bio-Rad) by SDS gel electrophoresis. Protein was transferred to a nitrocellulose membrane, blocked with 5% milk in TBST and probed with LC3B (Cell Signaling, 1:1000, overnight), p62/SQSTM-1 (Santa Cruz, 1:1000, 1 h), tubulin (Santa Cruz, 1:10000, 1 h), K63 ubiquitin (Cell Signaling, 1:1000, 1 h), K48 ubiquitin (Cell Signaling, 1:2000, 1 h) in 2% milk in TBST. Secondary labeling was performed with a one hour incubation in 1:20000 anti-rabbit HRP or 1:10000 anti-mouse HRP (Jackson Immunoresearch) diluted in 2% milk in TBST. Film was then exposed to ECL-coated blots (Pierce) and developed using a standard film processor.

What is claimed is:

1. A method for treating a disorder associated with Ras deregulation or dysregulation comprising administering to a subject in need of treatment an effective amount of a compound having the structure of Formula I, or a hydrate, isomer, prodrug or pharmaceutically acceptable salt thereof:

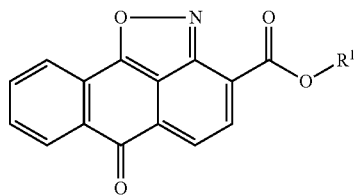

Formula I wherein $R^1$ is a branched or straight chain, alkyl or alkenyl radical with 1 to 18 carbon atoms.

2. The method of claim 1, wherein $R_1$ is a branched or straight chain alkyl radical with 1 to 6 carbon atoms.

3. The method of claim 2, wherein the compound of Formula I is selected from the group consisting of:

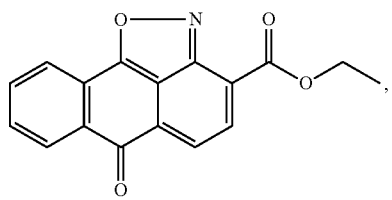

1

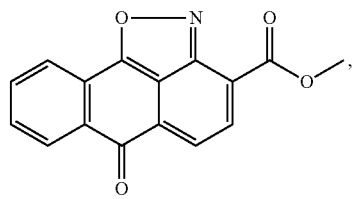

2 and pharmaceutically acceptable salts thereof.

4. The method of claim 3, wherein the compound of Formula I is:

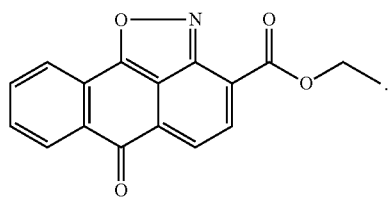

1

5. The method of claim 3, wherein the compound of Formula I is:

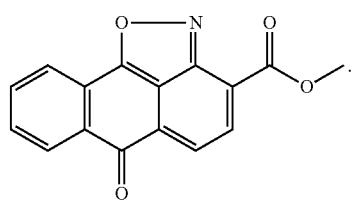

2

6. The method of claim 1, wherein said disorder associated with disorder associated with Ras deregulation or dysregulation comprises a disease state that results from a mutation or loss of function in a neurofibromin 1 gene.

7. The method of claim 1, wherein said disorder associated with disorder associated with Ras deregulation or dysregulation comprises Neurofibromatosis Type 1.

8. The method according to claim 1, wherein said disorder associated with Ras deregulation or dysregulation comprises neuroblastoma, lung adenocarcinoma, squamous cell carcinoma, glioblastoma, pancreatic cancer, ovarian cancer, colon cancer, lung cancer, neurofibromas, malignant peripheral nerve sheath tumor, optic glioma, Schwannoma, glioma, leukemia, pheochromocytoma or pancreatic adenocarcinoma.

9. The method according to claim 8, wherein the disorder associated with Ras deregulation or dysregulation is glioblastoma.

10. The method of claim 1, wherein the disorder associated with Ras deregulation or dysregulation is characterized by a mutation in K-Ras, H-Ras, N-Ras or R-Ras.

11. The method of claim 10, wherein the mutation is an activating mutation.

* * * * *